(12) United States Patent
Kurokawa et al.

(10) Patent No.: US 6,501,267 B1
(45) Date of Patent: Dec. 31, 2002

(54) EDDY-CURRENT FLAW DETECTOR PROBE

(75) Inventors: Masaaki Kurokawa, Hyogo (JP);
Mitsuyoshi Matsumoto, Hyogo (JP)

(73) Assignee: Mitsubishi Heavy Industries, Ltd.,
Tokyo (JP)

( * ) Notice: Subject to any disclaimer, the term of this patent is extended or adjusted under 35 U.S.C. 154(b) by 0 days.

(21) Appl. No.: 09/486,637

(22) PCT Filed: Aug. 5, 1999

(86) PCT No.: PCT/JP99/04232

§ 371 (c)(1),
(2), (4) Date: Feb. 29, 2000

(87) PCT Pub. No.: WO00/08458

PCT Pub. Date: Feb. 17, 2000

(30) Foreign Application Priority Data

Aug. 6, 1998 (JP) .............................. 10-223014

(51) Int. Cl.⁷ ..................... G01N 27/90; G01R 33/12
(52) U.S. Cl. ........................... 324/242; 324/262
(58) Field of Search ................ 324/242, 238, 324/239, 240, 241, 243, 262; 336/232

(56) References Cited

U.S. PATENT DOCUMENTS

| 3,281,667 A | * | 10/1966 | Dobbins et al. | ............ | 324/241 |
| 5,047,719 A | * | 9/1991 | Johnson et al. | ............. | 324/242 |
| 5,389,876 A | | 2/1995 | Hedengren et al. | | |
| 5,659,248 A | * | 8/1997 | Hedengren et al. | ......... | 324/242 |

FOREIGN PATENT DOCUMENTS

| CA | 2240045 | 4/1998 |
| JP | 57-182163 | 11/1982 |
| JP | 9-107258 | 6/1984 |
| JP | 62-245152 | 10/1987 |
| JP | 63-180850 | 7/1988 |
| JP | 3002846 | 7/1994 |
| JP | 6-65858 | 9/1994 |
| JP | 7-83884 | 3/1995 |
| JP | 7-34366 | 6/1995 |
| JP | 7-333199 | 12/1995 |
| JP | 9-33488 | 2/1997 |
| JP | 9-152423 | 6/1997 |
| JP | 10-2883 | 1/1998 |
| JP | 10-111279 | 4/1998 |
| JP | 2577684 | 5/1998 |
| JP | 10-197493 | 7/1998 |
| JP | 10-282065 | 10/1998 |
| JP | 10-300726 | 11/1998 |
| JP | 11-14600 | 1/1999 |
| JP | 11-51905 | 2/1999 |
| JP | 11-51906 | 2/1999 |

\* cited by examiner

*Primary Examiner*—Walter E. Snow
(74) *Attorney, Agent, or Firm*—Armstrong, Westerman & Hattori, LLP

(57) ABSTRACT

The present invention relates to an eddy current testing probe, which is suitable for used in a nondestructive test. The eddy current testing probe is provided with an excitation coil (2, 2a, 2b) which generates an alternating magnetic field to generate an eddy current (12) in a specimen (10), and a pair of detection coils (1a, 1b) differentially connected and arranged in phase. A central portion (C1) of the pair of detection coils and a central portion (C2) of the excitation coil (2, 2a, 2b) are arranged to be located at an identical or an almost identical position in a plan view taken in the direction toward the specimen (10), and a flaw (11) on the specimen (10) is detected based on a difference between voltages generated in the pair of detection coils (1a, 1b) due to the eddy current (12).

24 Claims, 12 Drawing Sheets

COILS 1a AND 1b ARE
DIFFERENTIALLY CONNECTED

DETECTION OF FLAW BY CONVENTIONAL
TECHNIQUE WHEN TILTED LIFT-OFF OCCURS

EXAMPLE OF SELFINDUCTION TYPE

EXAMPLE OF MUTUAL INDUCTION TYPE

EXAMPLE OF TWO-ROW ARRANGEMENT

DIRECTION OF MOVEMENT

EDDY-CURRENT FLAW DETECTOR PROBE

TECHNICAL FIELD

The present invention relates to an eddy current testing probe which is usable in nondestructive testing.

BACKGROUND ART

Eddy current testing probes have been developed for use in nondestructive testing, which are performed, for example, during manufacturing of steel or nonferrous products or maintenance of heat exchanger tubes in various plants. Basically, testing of a specimen by using an eddy current testing probe is performed by generating an eddy current at a surface of the specimen by an excitation coil, and monitoring change in impedance of a detection coil due to an influence of the eddy current to detect a flaw. When a flaw exists at the surface of the specimen, the flaw affects the eddy current generated at the surface of the specimen. When the eddy current changes, an influence of the change in the eddy current appears in the impedance of the detection coil. Therefore, the flaw in the specimen can be detected by monitoring the change in the impedance of the detection coil.

FIGS. 7(a) to 7(d) are schematic diagrams illustrating the constructions of various types of conventional eddy current testing probes, where the eddy current testing probes can be sorted into the respective types based on their modes of detection of the change in the impedance and their constructions of the excitation coils and the detection coils.

Based on the modes of detection of the change in the impedance, the eddy current testing probes can be sorted into an absolute type and a differential type. The eddy current testing probe of the absolute type detects the flaw in the specimen by a detection coil, as illustrated in FIGS. 7(a) and 7(b), and the eddy current testing probe of the differential type detects the flaw in the specimen based on a difference between amounts of impedance generated in a pair of detection coils, as illustrated in FIGS. 7(c) and 7(d).

Based on the constructions of the excitation coils and the detection coils, the eddy current testing probes can be sorted into a selfinduction type as illustrated in FIGS. 7(a) and 7(c), and a mutual-induction type as illustrated in FIGS. 7(b) and 7(d). In the eddy current testing probe of the selfinduction type, a single coil functions as both of an excitation coil and a detection coil, where the excitation coil generates an eddy current, and the detection coil detects impedance. In the eddy current testing probe of the mutual-induction type, an excitation coil (primary coil) and a detection coil (secondary coil) are provided separately.

As described above, the eddy current testing probes can be sorted into the four types as illustrated in FIGS. 7(a) to 7(d), according to their modes of detection of the change in the impedance of the detection coil and their constructions of the excitation coils and the detection coils.

The basic constructions and operations of the eddy current testing probes illustrated in FIGS. 7(a) to 7(d) are explained below.

In the eddy current testing probe of the absolute and selfinduction type as illustrated in FIG. 7(a), an excitation and detection coil 59 which functions both of the excitation coil and the detection coil is arranged to face a specimen (a planar object to be tested) 10. An oscillator (not shown) and an instrument (not shown) for monitoring the impedance are connected to the excitation and detection coil 59. The oscillator is provided for supplying an alternating current to the excitation and detection coil 59.

In order to detect a flaw in the specimen 10 by using the eddy current testing probe having the above construction, first, an alternating current from the oscillator is supplied to the excitation and detection coil 59 for generating an alternating magnetic field as illustrated by the arrows F1 and F2, so that an eddy current is generated at the surface of the specimen 10. Thus, impedance corresponding to the eddy current is generated in the excitation and detection coil 59. If a flaw exists at the surface of the specimen 10, the eddy current changes, and thus the impedance of the excitation and detection coil 59 also changes. Therefore, the flaw in the specimen 10 can be detected by monitoring the impedance of the excitation and detection coil 59.

In the eddy current testing probe of the absolute and mutual-induction type as illustrated in FIG. 7(b), a detection coil 51 and an excitation coil 52 are arranged so that the detection coil 51 and the excitation coil 52 face the specimen 10, and are adjacent to each other. An instrument (not shown) for monitoring the impedance is connected to the detection coil 51, and an oscillator (not shown) is connected to the excitation coil 52.

In the above construction, an alternating magnetic field as illustrated by the arrows F3 and F4 is generated by the excitation coil 52 so that an eddy current is generated at the surface of the specimen 10. Then, impedance generated by the eddy current in the detection coil 51 is monitored to detect the flaw.

In the eddy current testing probe of the differential and selfinduction type as illustrated in FIG. 7(c), the excitation and detection coils 59a and 59b forming a pair are arranged at the same distance from the specimen 10 to face the specimen 10. An oscillator (not shown) is connected to each of the excitation and detection coils 59a and 59b for supplying an alternating current to the excitation and detection coils 59a, 59b. In addition, an instrument (not shown) for monitoring a difference between amounts of the impedance generated in the excitation and detection coils 59a and 59b is connected to both the excitation and detection coils 59a and 59b.

When detecting a flaw in the specimen 10 by using the eddy current testing probe having the above construction, first, an alternating current from the oscillator is supplied to the excitation and detection coils 59a and 59b to generate an alternating magnetic field as illustrated by the arrows F5 and F6 by the excitation and detection coil 59a and an alternating magnetic field as illustrated by the arrows F7 and F8 by the excitation and detection coil 59b, so that eddy currents are generated at the surface of the specimen 10. At this time, impedance is generated in each of the excitation and detection coils 59a and 59b corresponding to the eddy current. When no flaw exists at the surface of the specimen 10, the state of the surface is uniform, and the distribution of the eddy current generated at the surface of the specimen 10 is also uniform. Therefore, amounts of the impedance generated in the respective excitation and detection coils 59a and 59b are identical. On the other hand, if a flaw exists at the surface of the specimen 10, the distribution of the eddy current generated at the surface of the specimen 10 is not uniform due to the existence of the flaw. Therefore, amounts of the impedance generated in the respective excitation and detection coils 59a and 59b become different. Thus, the flaw can be detected by monitoring a difference between the amounts of the impedance generated in the excitation and detection coils 59a and 59b.

In the eddy current testing probe of the differential and mutual-induction type as illustrated in FIG. 7(d), an excitation coil 52 and a pair of detection coils 51a and 51b are arranged to face the specimen 10, where the pair of detection coils 51a and 51b is located nearer to the specimen 10 than the excitation coil 52. An oscillator (not shown) is connected to the excitation coil 52, and an instrument (not shown) for monitoring a difference between amounts of the impedance generated in the detection coils 51a and 51b is connected to the detection coils 51a and 51b. The detection coils 51a and 51b are arranged at the same distance from the specimen 10 so that the detection coils 51a and 51b are symmetrically located with respect to a centerline of the excitation coil 52 in a plan view seen from the top of FIG. 7(d), and are located at equivalent positions relative to the specimen 10 and the excitation coil 52. That is, the detection coils 51a and 51b are arranged under the equivalent conditions with respect to the eddy current generated in the specimen 10 by the excitation coil 52.

In the above construction, a flaw can be detected by generating an alternating magnetic field as illustrated by the arrows F9 and F10 to generate an eddy current at the surface of the specimen 10, and monitoring a difference between amounts of impedance generated in the detection coils 51a and 51b corresponding to the eddy current.

Incidentally, in order to efficiently detect a flaw, a multi-coil eddy current testing probe is proposed. In the multicoil eddy current testing probe, a plurality of detection coils or excitation and detection coils as above are arranged in a row, for example, in the direction of the width of the specimen 10. FIG. 9 shows a multicoil eddy current testing probe 20a of the selfinduction type, in which a plurality (five, in the illustrated example) of excitation and detection coils 59a to 59e are arranged in a row, and FIG. 10 shows another multicoil eddy current testing probe 20b of the mutual-induction type, in which a plurality (five, in the illustrated example) of excitation coils 52a to 52e and a plurality (tens in the illustrated example) of detection coils 51a to 51j are arranged in rows.

When the above plurality of coils in the multicoil eddy current testing probe 20a or 20b are arranged corresponding to the width of the specimen 10, and the multicoil eddy current testing probe 20a or 20b is moved in the direction over the specimen 10 as illustrated by the arrows A1 in FIG. 9 or B1 in FIG. 10, a relatively wide range of the specimen can be examined at a time, even if the specimen 10 is a flat plate of great width.

For example, coils having a shape of a bobbin or pancake are usually used as the above detection coils, excitation coils, and excitation and detection coils.

However, impedance generated in a detection coil varies with a distance between the detection coil and the specimen. Therefore, if the distance between the detection coil and the specimen varies (as lift-off), the impedance of the detection coil changes corresponding to the lift-off, even if no flaw exists. (At this time, the change in the impedance is called a lift-off signal.) Thus, there is a problem that the conventional eddy current testing probe cannot accurately detect a flaw due to the lift-off signal.

In the eddy current testing probes of the absolute type, which detect a flaw of a specimen by a single detection coil as illustrated in FIGS. 7(a) and 7(b), impedance generated in the excitation and detection coil 59 or the detection coil 51, per se, is monitored by an impedance monitor circuit. Therefore, when lift-off occurs between the eddy current testing probe and the specimen, impedance of the coil caused by the lift-off, i.e., the lift-off signal, is noise. Thus, the impedance which can be measured by the impedance monitor circuit is affected by the lift-off signal, and therefore it is impossible to accurately detect a flaw.

In addition, in the eddy current testing probes of the differential type as illustrated in FIGS. 7(c) and 7(d), a flaw of a specimen is detected based on a difference between amounts of impedance generated in two detection coils. For example, in the eddy current testing probe of the differential and mutual-induction type as illustrated in FIG. 7(d), as long as the distance $l_1$ between the detection coil 51a and the specimen 10 and the distance 12 between the detection coil 51b and the specimen 10 are equal, amounts of impedance generated in the detection coils 51a and 51b are identically changed even when the distances $l_1$ and $l_2$ vary. That is, a difference between amounts of impedance generated in two detection coils is not affected by the distance $l_1$, $l_2$ (normally $l_1=l_2$). Therefore, when the two detection coils 51a and 51b lift off, maintaining the parallelism with the specimen, i.e., when the two detection coils 51a and 51b lift off in a parallel lift-off mode, the flaw of the specimen 10 can be accurately detected without influence of the parallel lift-off.

However, when the two detection coils 51a and 51b lift off in a tilted lift-off mode, the row of the two detection coils 51a and 51b tilts with respect to specimen 10, i.e., when the distances $l_1$ and $l_2$ become different, as illustrated in FIG. 8, the amounts of impedance generated in the two detection coils 51a and 51b becomes different corresponding to the distances 11 and 12. Therefore, a difference between the changes in the amounts of the impedance generated in the two detection coils 51a and 51b arises as a lift-off signal, and a flaw cannot be detected accurately.

Although the above problem is explained for the eddy current testing probe of the differential and mutual induction type as an example, the eddy current testing probe of the differential and selfinduction type has the same problem.

FIGS. 11(a) and 11(b) shows a distribution of detectivity of the excitation and detection coils 59a and 59b in the multicoil-type eddy current testing probe as illustrated in FIG. 9. FIG. 11(a) is a diagram illustrating a geometrical relationship between the excitation and detection coils 59a and 59b and a flaw 11, and FIG. 11(b) is a diagram illustrating amplitudes (signal levels) of detection signals obtained by the excitation and detection coils 59a and 59b. In FIG. 11(b), the abscissa indicates a distance L from a reference line CL0 which is located at the center of the axis centerlines of the excitation and detection coils 59a and 59b, and the ordinate indicates a signal level detected by each of the excitation and detection coils 59a and 59b when the flaw is located at the position of the abscissa. Curves Lx and Ly show distributions of detectivity by the excitation and detection coils 59a and 59b, respectively. The signal level of the excitation and detection coil 59a is maximized when the flaw 11 is located just below the excitation and detection coil 59a, i.e., the flaw 11 is located on the axis centerline CLx of the excitation and detection coil 59a. Therefore, the distribution curve Lx of detectivity of the excitation and detection coil 59a has the maximum on the axis centerline CLx. Similarly, the distribution curve Ly of detectivity of the excitation and detection coil 59b has the maximum on the axis centerline CLy.

There is a low-detection-level region (a region in which the detection level is low) between the excitation and detection coils 59a and 59b. Therefore, when a flaw 11 is located in the vicinity of the reference line CL0, the flaw 11 may not be accurately detected by the multicoil eddy current testing probe 20a or 20b as illustrated in FIGS. 9 and 10, in which a plurality of detection coils or excitation and detection coils are arranged in only one row.

The low-detection-level region can be reduced by decreasing the distances between the adjacent detection coils or excitation and detection coils. Therefore, in order to reduce the low-detection-level region (to flatten the distribution of detectivity of a flaw signal), a multicoil eddy current testing probe 20c of the two-row selfinduction type as illustrated in FIG. 12 is proposed. In the eddy current testing probe 20c, a plurality (nine, in the illustrated example) of excitation and detection coils 59f to 59n are arranged in two rows, and the positions of the excitation and detection coils 59f to 59i in the first row located on the front side are relatively shifted from the positions of the excitation and detection coils 59j to 59n in the second row located on the rear side in the direction of the width (i.e., in the direction perpendicular to the direction of movement of the multicoil eddy current testing probe 20c) so as to decrease distances between adjacent excitation and detection coils, and thus flatten the detection level distribution of the flaw signal.

Incidentally, it is effective to produce a perspective view as illustrated in FIG. 13 for evaluating the shape of a flaw intuitively and accurately. In FIG. 13, the X-axis and Y-axis indicate a two-dimensional position on the specimen 10, and the Z-axis indicates the level of a detection value detected by the multicoil eddy current testing probe at each point indicated by the X-Y coordinates. However, it is very difficult to produce the perspective view based on the detection result by the multicoil eddy current testing probe 20c.

Since, in the eddy current testing probe 20c, the plurality of excitation and detection coils 59f to 59n are arranged in two rows in the direction perpendicular to the direction of movement of the multicoil eddy current testing probe 20c, the excitation and detection coils 59f to 59i in the first row and the excitation and detection coils 59j to 59n in the second row perform detection at different positions in the direction of movement of the multicoil eddy current testing probe 20c at the simultaneous detection. That is, there are gaps between the positions of detection. The correspondences between two-dimensional positions on the specimen 10 and the detection values at the two-dimensional positions are essential for producing a perspective view as illustrated in FIG. 13, and therefore it is necessary to correct the detection values with respect to positions, taking the above gaps into consideration. However, the moving speed of the multicoil eddy current testing probe 20c also varies. Therefore, the above gaps vary, and thus, it is very difficult to accurately correct the detection values with respect to positions.

DISCLOSURE OF THE INVENTION

An object of the present invention is to provide an eddy current testing probe which can detect a flaw accurately.

In order to accomplish the above-mentioned object, an eddy current testing probe according to the present invention contains an excitation coil which generates an alternating magnetic field to generate an eddy current in a specimen; and a pair of detection coils differentially connected and arranged in phase. A central portion of the pair of detection coils and a central portion of the excitation coil are arranged to be located at an identical or an almost identical position in a plan view taken in the direction toward the specimen, and a flaw on the specimen is detected based on a difference between voltages generated in the pair of detection coils due to the eddy current.

When the eddy current testing probe is constructed as above, even if distances from the respective detection coils to the specimen are different, a sum of magnetic fluxes which are generated by the eddy current, and act on the detection coils is not changed. Therefore, the flaw on the specimen can be accurately detected based on the difference between voltages generated in the pair of detection coils by the magnetic fluxes, even in the case wherein the detection coils moves in the tilted lift-off mode in which a difference arises between the distances from the detection coils to the specimen, in addition to the case of the parallel lift-off mode in which the parallelism between the detection coils and the specimen is maintained.

In addition, it is preferable that the eddy current testing probe is configured so that the excitation coil generates the eddy current in a slanting direction with respect to the direction of the flaw on the specimen.

When the eddy current testing probe is configured like this, i.e., when the eddy current testing probe is configured so that the excitation coil generates the eddy current in a slanting direction with respect to the direction of the flaw on the specimen, the eddy current is effectively influenced by the flaw on the specimen, and thus the flaw on the specimen can be detected further accurately.

Further, it is preferable that the detection coils in the pair in the eddy current testing probe are arranged on a plane, side by side, and symmetrically with respect to a line.

When the eddy current testing probe is constructed like this, i.e., when the detection coils in the pair in the eddy current testing probe are arranged on a plane, side by side, and symmetrically with respect to a line, the detection coils are under equivalent conditions concerning the eddy current, and thus the flaw on the specimen can be detected further accurately.

Furthermore, it is preferable that the eddy current testing probe contains a bridge circuit which is connected to the pair of detection coils for obtaining as a flaw signal the difference between voltages generated in the pair of detection coils due to the eddy current.

In this construction, the flaw can be automatically detected by the bridge circuit.

Otherwise, in order to accomplish the aforementioned object, an eddy current testing probe to detect a flaw on the specimen according to the present invention contains a plurality of excitation coils which generate an alternating magnetic field to generate an eddy current in a specimen; and a plurality of thin-film detection coils which are arranged in upper and lower layers in a row.

Since the above eddy current testing probe contains a plurality of thin-film detection coils which are arranged in upper and lower layers in a row, it is not necessary to correct detection values with respect to positions in the up-and-down direction and in the direction of movement of the eddy current testing probe, i.e., in the directions perpendicular to the direction of the row. That is, it is not necessary to correct detection values between the detection coils in the upper layer and the detection coils in the lower layer. Therefore, the flaw on the specimen can be detected accurately.

In the above eddy current testing probe, it is preferable that the positions of the detection coils in the upper layer are relatively shifted by about a half pitch from the positions of the detection coils in the lower layer.

When the eddy current testing probe is constructed like this, i.e., when the positions of the detection coils in the upper layer are relatively shifted by about a half pitch from the positions of the detection coils in the lower layer, it is possible to reduce the distances between adjacent ones of the plurality of thin-film detection coils, and thus flatten a distribution of detectivity of the eddy current testing probe as a whole. Therefore, the flaw on the specimen can be detected further accurately.

In addition, it is preferable that a thin-film insulation layer is inserted between the upper layer and the lower layer.

When the eddy current testing probe is constructed like this, i.e., a thin-film insulation layer is inserted between the upper layer and the lower layer, it is possible to prevent interaction between the detection coils in the upper layer and the detection coils in the lower layer. Therefore, the flaw on the specimen can be detected further accurately.

Further, it is preferable that the above insulation layer has a through hole for leading out a signal wire of each detection coil in the lower layer.

Since a signal wire of each detection coil in the lower layer can be led to the upper side through the through hole provided in the insulation layer, it is unnecessary to provide space for a signal wire on the underside of the detection coils, and therefore it is possible to put the eddy current testing probe closer to the specimen, and suppress attenuation of a flaw signal. Thus, the flaw on the specimen can be detected further accurately. In addition, since the signal wire, which is conductive, is not arranged between the detection coils in the lower layer and the specimen, accuracy of the detection by the detection coils is not degraded.

Furthermore, in the above eddy current testing probe, preferably, each of the above excitation coils may be realized by a circular coil having a small length in the direction of the axis thereof and being arranged to stand almost perpendicularly to the surface of the specimen, and the above plurality of excitation coils may be arranged in one or more rows above the plurality of thin-film detection coils.

When the eddy current testing probe is constructed like this, i.e., when each of the above excitation coils is realized by a circular coil having a small length in the direction of the axis thereof and being arranged to stand almost perpendicularly to the surface of the specimen, and the above plurality of excitation coils are arranged in one or more rows above the plurality of thin-film detection coils, spatially dense probe configuration is realized, and efficient excitation is enabled. In addition, downsizing of the eddy current testing probe can be realized, and therefore handleability of the eddy current testing probe is enhanced.

In addition, it is preferable to construct the eddy current testing probe so that each excitation coil is oriented in a slanting direction with respect to the direction of the row of the plurality of excitation coils.

When the eddy current testing probe is constructed like this, i.e., when each excitation coil is oriented in a slanting direction with respect to the direction of the row of the plurality of excitation coils, further downsizing of the eddy current testing probe can be realized, and therefore handleability of the eddy current testing probe is further enhanced.

Further, it is preferable to construct the eddy current testing probe so that voltages are not applied concurrently to adjacent ones of the plurality of excitation coils.

When the eddy current testing probe is constructed like this, i.e., when voltages are not applied concurrently to adjacent ones of the plurality of excitation coils, it is possible to prevent interaction between eddy currents which are concurrently generated at adjacent positions. Therefore, the flaw on the specimen can be detected further accurately.

Furthermore, it is preferable that the above voltages are applied to the excitation coils in a pulsed mode.

In addition, it is preferable to construct the eddy current testing probe so as to move along the surface of the specimen in the direction perpendicular to the direction of the rows of the plurality of thin-film detection coils, and detect a flaw at the surface of the specimen.

When the eddy current testing probe is constructed like this, i.e., the eddy current testing probe moves along the surface of the specimen in the direction perpendicular to the direction of the rows of the plurality of thin-film detection coils, and detects a flaw at the surface of the specimen, it is possible to detect a flaw over a wide range.

BEST MODE FOR CARRYING OUT THE INVENTION

The embodiments of the present invention are explained below with reference to the drawings.

Figure 2:
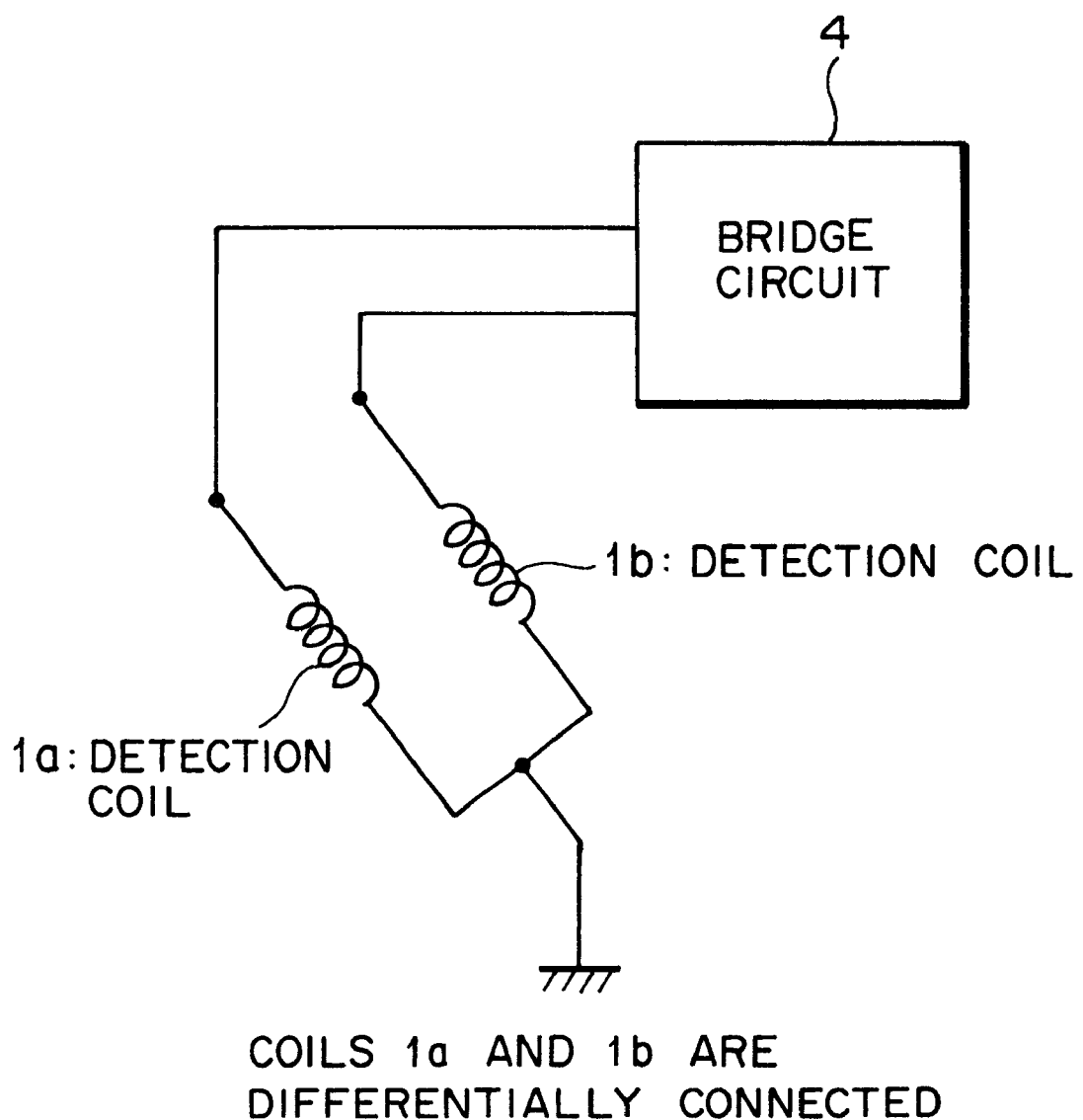
FIG. 2 is a diagram illustrating a construction of a circuit containing a bridge circuit and detection coils in the first embodiment of the present invention.
Figure 3:
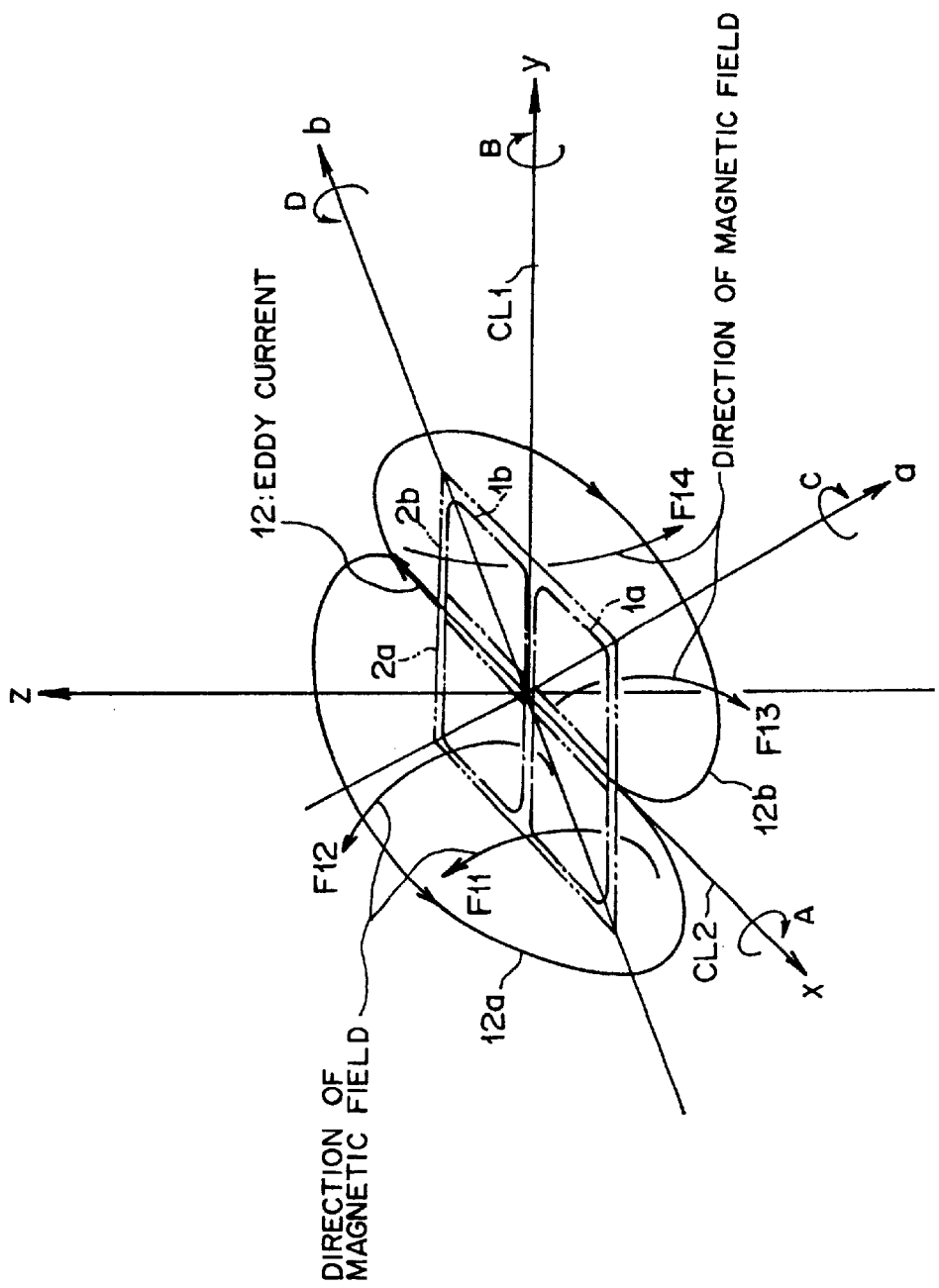
FIG. 3 is a diagram illustrating geometrical relationship of eddy currents, flux linkages, the excitation coil, and the detection coils, where the single-dot chain line indicates the position of the detection coils in a plan view in the direction toward the specimen, and the two-dot chain line indicates the position of the excitation coil in the plan view.
Figure 4A:
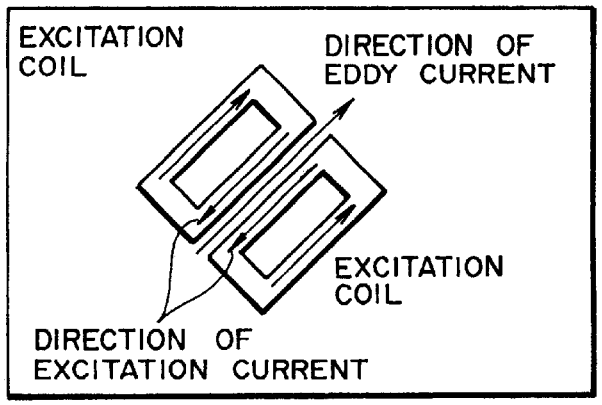
FIG. 4(a) is a diagram illustrating a planar excitation coil used in the eddy current testing probe as the first embodiment of the present invention.
Figure 4B:
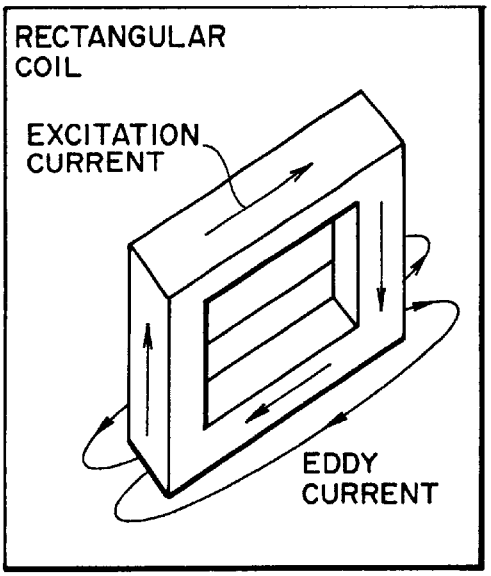
FIG. 4(b) is a diagram illustrating a rectangular excitation coil.
Figure 4C:
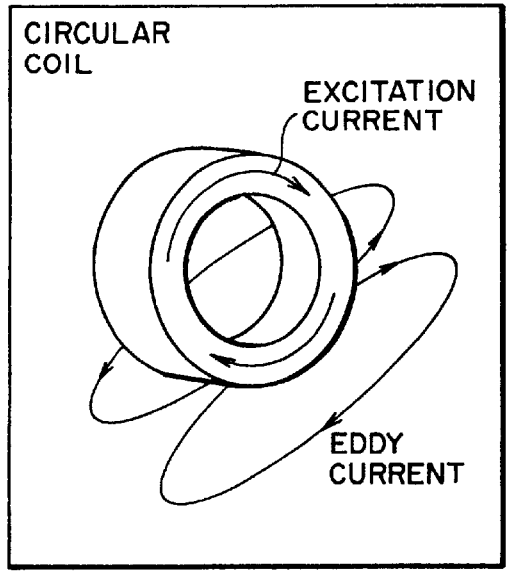
FIG. 4(c) is a diagram illustrating a circular excitation coil.

First, explanations are provided for the first embodiment. FIGS. 1(a) to 4(c) relate to the eddy current testing probe as the first embodiment of the present invention. FIGS. 1(a) to 1(d) show the main portion of and eddy currents in the first embodiment, FIG. 2 shows the construction of the circuit containing the bridge circuit and detection coils, FIG. 3 shows geometrical relationship of eddy currents, flux linkages, the excitation coil, and the detection coils, and FIGS. 4(a) to 4(c) show various types of excitation coils.

The eddy current testing probe as the present embodiment moves over the specimen 10, and detects a flaw 11 when the flaw 11 is located under the eddy current testing probe. The eddy current testing probe contains an excitation coil 2 which generates an alternating magnetic field to generate an eddy current 12 on the specimen 10, a pair of detection coils 1a and 1b arranged in phase and differentially connected, and a bridge circuit 4 connected to the pair of detection coils 1a and 1b. In addition, the excitation coil 2 is connected to an oscillator 3, which supplies an alternating current to the excitation coil 2. The pair of detection coils 1a and 1b are arranged at the same distance from the specimen (planar object to be tested) 10.

The circuit construction of the present eddy current testing probe is explained below. As illustrated in FIG. 2, a pair of detection coils 1a and 1b, which are differentially connected, are connected to the bridge circuit 4, so that a flaw signal is output from the bridge circuit 4 when voltages generated in the detection coils 1a and 1b are different.

Figure 1A:
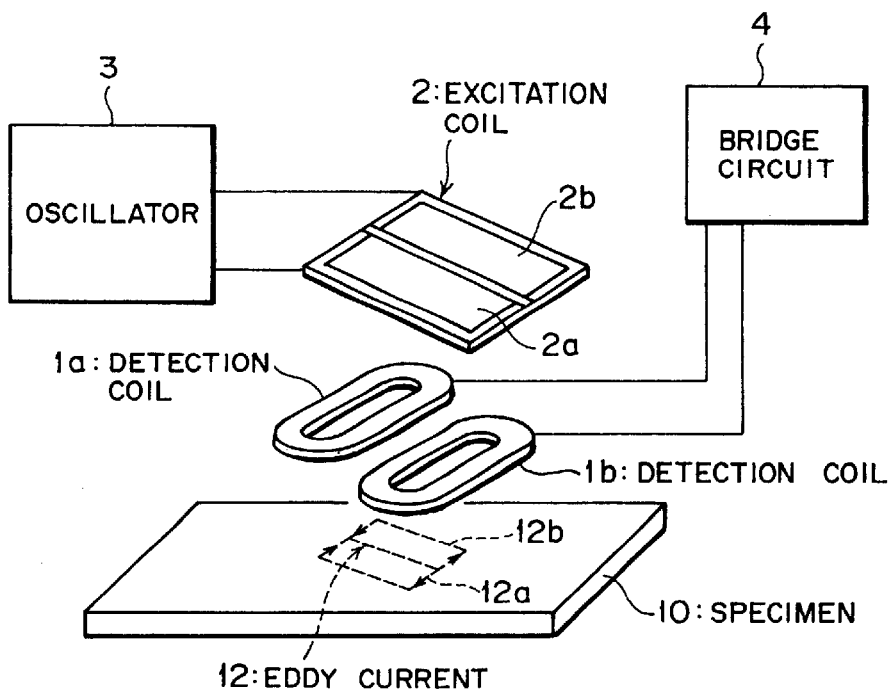
FIG. 1(a) is a schematic diagram illustrating the construction of the main portion of the eddy current testing probe as the first embodiment of the present invention.
Figure 1B:
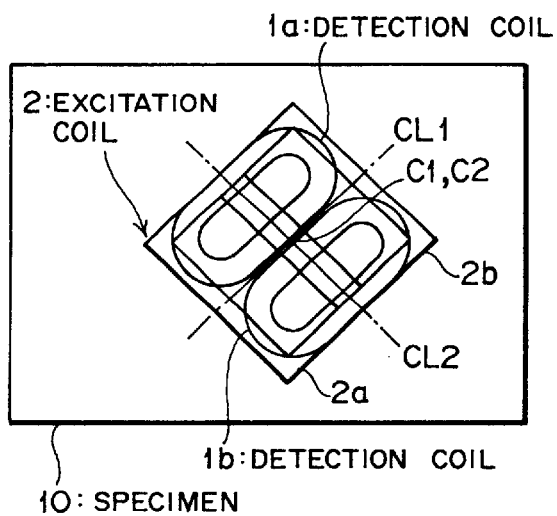
FIG. 1(b) is a schematic diagram illustrating geometrical relationship of the essential portion of the eddy current testing probe in a plan view as the first embodiment of the present invention.
Figure 1C:
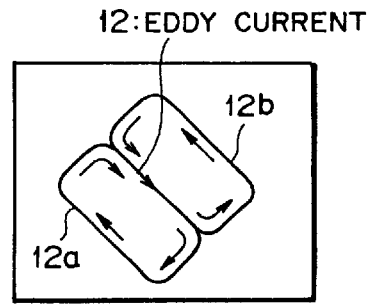
FIG. 1(c) is a diagram illustrating a state of eddy currents under the eddy current testing probe as the first embodiment of the present invention when no flaw exists in the specimen.
Figure 1D:
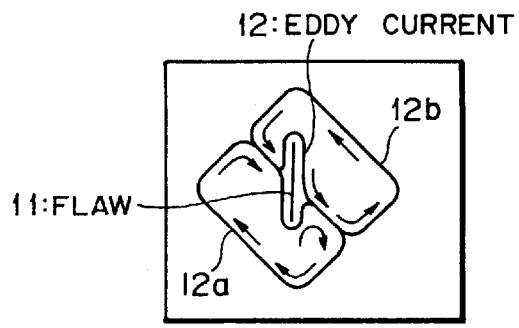
FIG. 1(d) is a diagram illustrating a state of eddy currents under the eddy current testing probe as the first embodiment of the present invention when a flaw exists in the specimen.

The excitation coil 2 is formed by arranging a pair of identical coils 2a and 2b on a plane, side by side, and symmetrically with respect to a line, so that a pair of eddy currents 12a and 12b are generated, where the pair of eddy currents 12a and 12b are located side by side and symmetrically with each other, as illustrated in FIGS. 1(a), 1(c), and 1(d). In particular, a strong eddy current 12 is generated on the line of symmetry of the coils 2a and 2b due to summation of the eddy currents 12a and 12b.

In addition, as illustrated in FIG. 1(d), the excitation coil 2 is arranged in a direction such that the eddy current flows in a slanting direction with respect to a direction of a flaw which is expected when the flaw exists at the surface of the specimen 10. This is based on the principle of detection by the present eddy current testing probe. In the present eddy current testing probe, a flaw 11 is detected by utilizing the fact that the flaw 11 at the surface of a specimen 10, as an external disturbance, changes the eddy current 12 as illustrated in FIG. 1(d). Therefore, if the flaw 11 is along the flow of the eddy current 12, i.e., if the flaw 11 is parallel to the flow of the eddy current 12, it is not easy for the flaw 11 to act as a prominent external disturbance on the eddy current 12. In addition, the direction of the flaw at the surface of the specimen 10 can be appropriately expected from a manufacturing process of the specimen 10 or the like.

Incidentally, as illustrated in FIG. 1(a), the detection coils 1a and 1b are arranged on a plane, side by side, and symmetrically with respect to a line, and parallel to the specimen 10. In addition, as illustrated in FIG. 1(b), the detection coils 1a and 1b are arranged so that the line CL1 of symmetry of the detection coils 1a and 1b is perpendicular to the centerline (the centerline of symmetry of the excitation coils 2a and 2b) CL2 in the plan view. In addition, the detection coils 1a and 1b are arranged so that the center portion C1 (which is located on the line CL1 of symmetry) of the detection coils 1a and 1b and the center portion C2 (which is located on the line CL2 of symmetry) of the excitation coil 2 coincide in the plan view.

The eddy current 12 is generated at the surface of the specimen 10, on the centerline CL2 of the excitation coil 2 in the plan view of FIG. 1(b). In particular, the eddy current 12 is surely generated around the center portion C2 of the excitation coil 2, and therefore the center portion C1 of the detection coils 1a and 1b is located just above the location at which the eddy current is most surely generated.

Although, in the illustrated example, the line CL1 of symmetry of the detection coils 1a and 1b and the line CL2 of symmetry of the excitation coil 2 cross at right angles in the plan view, it is not necessary for the centerlines CL1 and CL2 to cross at right angles. It is sufficient for the centerlines CL1 and CL2 to cross. In addition, although the center portion C1 of the detection coils 1a and 1b and the center portion C2 of the excitation coil 2 coincide in the plan view, it is not necessary for the center portions C1 and C2 to coincide. It is sufficient for the center portions C1 and C2 to be close together. However, for ease and accuracy of detection, the configuration of the present embodiment is preferable.

Since the eddy current testing probe as the first embodiment is constructed as above, a pair of eddy currents 12a and 12b are generated on the specimen 10 corresponding to the configuration of the coils 2a and 2b, an upward flux linkages as indicated by the arrows F11 and F12 are generated due to the eddy current 12a, and downward flux linkages as indicated by the arrows F13 and F14 are generated due to the eddy current 12b, as illustrated in FIG. 3. Since the center portion C1 of the detection coils 1a and 1b and the center portion C2 of the excitation coil 2 coincide in the plan view, and the orientations of the detection coils 1a and 1b (the orientation of the line CL1 of symmetry of the detection coils 1a and 1b) are perpendicular to the orientations of the excitation coils 2a and 2b (the orientation of the line CL2 of symmetry of the excitation coils 2a and 2b) in the plan view, similar geometrical relationships exist between the detection coils 1a and 1b and the eddy currents 12a and 12b.

Therefore, the upward flux linkages as indicated by the arrows F11 and F12 act on the one halves (on the left halves in FIG. 3) of the detection coils 1a and 1b, and the downward flux linkages as indicated by the arrows F13 and F14 act on the other halves (on the right halves in FIG. 3) of the detection coils 1a and 1b. This is, flux linkages of opposite directions act on the right and left halves of each of the detection coils 1a and 1b.

When no flaw exists on the specimen 10, no external disturbance acts on the eddy currents 12a and 12b, as illustrated in FIG. 1(c). Therefore, in this case, no difference arises between the flux linkages acting on the respective detection coils 1a and 1b, and thus no difference arises between the voltages generated in the detection coils 1a and 1b according to the flux linkages, respectively. Consequently, no flaw signal is generated by the bridge circuit 4. On the other hand, when a flaw 11 exists on the specimen 10, an external disturbance acts on the eddy currents 12a and 12b, as illustrated in FIG. 1(d). Therefore, the flux linkages generated by the eddy currents 12a and 12b have uneven distributions, and thus a difference arises between a sum of flux linkages acting on the detection coil 1a and a sum of flux linkages acting on the detection coil 1b. Consequently, a difference arises between the voltages generated in the detection coils 1a and 1b, and thus a flaw signal is output from the bridge circuit 4 due to the voltage difference.

In addition, according to the present eddy current testing probe, no lift-off signal is generated by the lift-off.

Since, in the case of the-parallel lift-off, the detection coils 1a and 1b are located at the same distance from the specimen 10, the sums of flux linkages acting on the detection coils 1a and 1b are necessarily zero. Therefore, no difference occurs between the voltages generated in the detection coils 1a and 1b, and thus no lift-off signal is generated.

Also, in the case of the tilted lift-off, no or a negligible lift-off signal is generated. Explanations are provided below for the case of tilted lift-off due to rotations around the x-axis, y-axis, a-axis, and b-axis, as examples.

The flux linkages increase with decrease in the distance between the detection coil and the specimen 10. Therefore, when the detection coils 1a and 1b are rotated around the x-axis in the direction as indicated by the arrow A, the downward flux linkages F13 and F14 increase, and the upward flux linkages F11 and F12 decrease. Thus, the sum total of the flux linkages is directed downward. However, the sum of the flux linkages in each of the detection coils 1a and 1b is directed downward, and the amounts of the sums of the flux linkages in the detection coils 1a and 1b are identical. Therefore, voltages generated in the detection coils 1a and 1b, which are differentially connected, are identical, and thus no lift-off signal is generated.

Next, when the detection coils 1a and 1b are rotated around the y-axis in the direction as indicated by the arrow B, the flux linkages F11 and F13, which act on the detection coil 1a, decrease, and the flux linkages F12 and F14, which act on the detection coil 1b, increase. However, even when rotated, flux linkages F11 and F13 acting on the detection coil 1a are directed to opposite directions and have an identical amount. Therefore, the sum of the flux linkages acting on the detection coil 1a is zero. Similarly, the sum of the flux linkages acting on the detection coil 1b is zero. Thus, no lift-off signal is generated.

When the detection coils 1a and 1b are rotated around the a-axis in the direction as indicated by the arrow C, the downward flux linkage F14 increases, and the upward flux linkage F11 and decreases. Thus, the sum total of the flux linkages is directed downward. However, the sum of the flux linkages in each of the detection coils 1a and 1b is directed downward, and the difference between the amounts of the flux linkages in the detection coils 1a and 1b is small. Therefore, only a very weak lift-off signal is generated from the detection coils 1a and 1b which are differentially connected.

When the detection coils 1a and 1b are rotated around the b-axis in the direction as indicated by the arrow D, the upward flux linkage F12 increases, and the downward flux linkage F13 decreases. Thus, the sum total of the flux linkages is directed upward. However, the sum of the flux linkages in each of the detection coils 1a and 1b is directed upward, and the difference between the amounts of the flux linkages in the detection coils 1a and 1b is small. Therefore, only a very weak lift-off signal is generated from the detection coils 1a and 1b.

Thus, the eddy current testing probe of the present embodiment has the following advantages.

When a flaw exists on the surface of the specimen 10, a voltage difference is generated between the detection coil 1a and 1b, and the voltage difference can be detected by the bridge circuit 4 as a flaw signal.

Even if parallel or tilted lift-off occurs, such lift-off does not cause the detection coils 1a and 1b to generate a voltage difference (lift-off signal) having a level near the flaw signal.

Therefore, even if parallel or tilted lift-off occurs, it is possible to accurately detect a flaw.

Although, in the present embodiment, a pair of adjoining planar coils (called a planar excitation coil) are used as an excitation coil, as illustrated in FIG. 4(a), for example, a rectangular coil (called a rectangular excitation coil) as illustrated in FIG. 4(b), or a circular coil (called a circular excitation coil) as illustrated in FIG. 4(c), may be used by arranging such a coil to stand perpendicularly to the medium in which an eddy current is generated.

Otherwise, a flaw 11 may be detected by an operator who monitors a voltage difference between detection coils 1a and 1b by a voltmeter, which is provided instead of the bridge circuit 4.

Further, although the eddy current detection is performed by moving the above eddy current testing probe along the specimen 10, it is possible to form a multicoil eddy current testing probe by arranging in a row more than one eddy current testing probe as the present embodiment, so that detection can be performed over a wide area at a time.

Figure 5A:
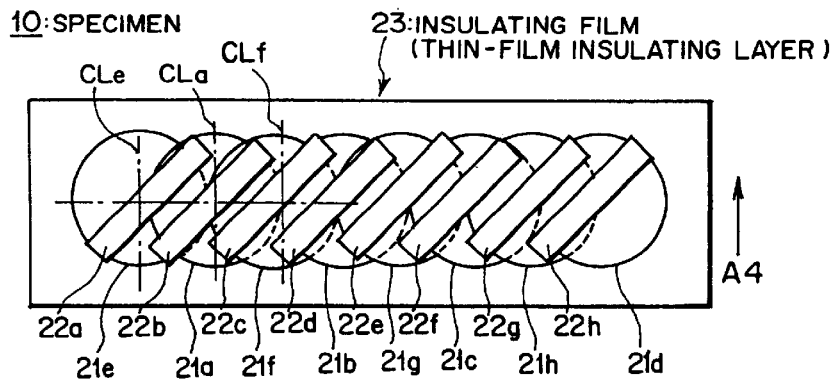
FIG. 5(a) is a plan view schematically illustrating the construction of the eddy current testing probe as the second embodiment of the present invention.
Figure 5B:
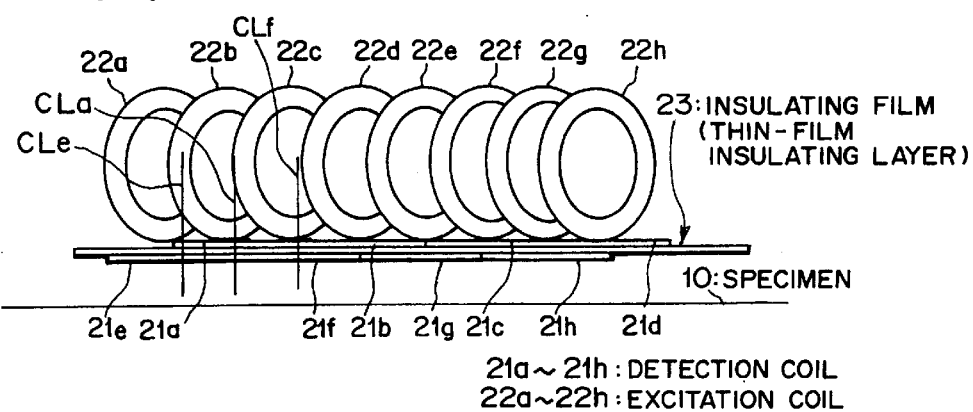
FIG. 5(b) is a front view schematically illustrating the construction of the eddy current testing probe as the second embodiment of the present invention, which is enlarged in the vertical direction.
Figure 5C:
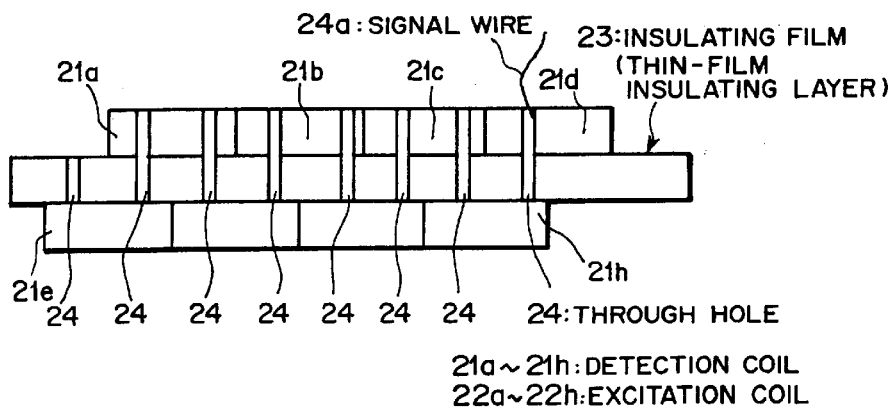
FIG. 5(c) is a crosssectional view schematically illustrating the essential portion of the eddy current testing probe as the second embodiment of the present invention, corresponding to the above front view, where the crosssectional view is greatly enlarged in the vertical direction.
Figure 6:
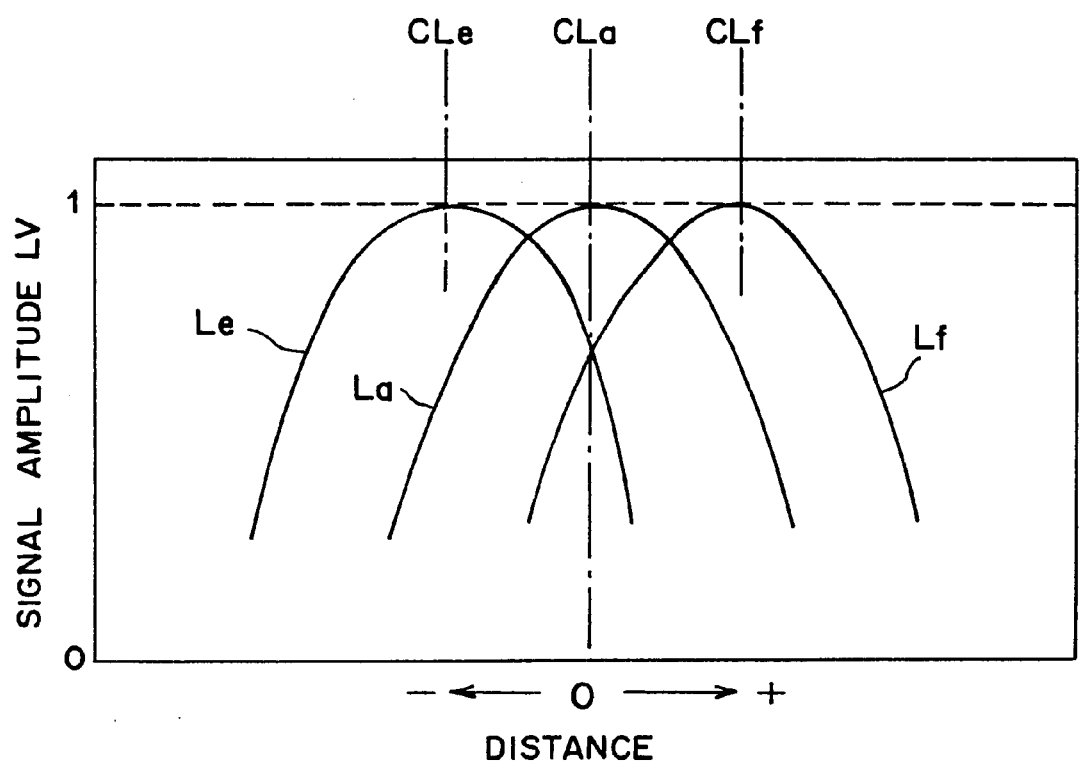
FIG. 6 is a diagram illustrating a distribution of detectivity of the eddy current testing probe as the second embodiment of the present invention.
Figure 7A:
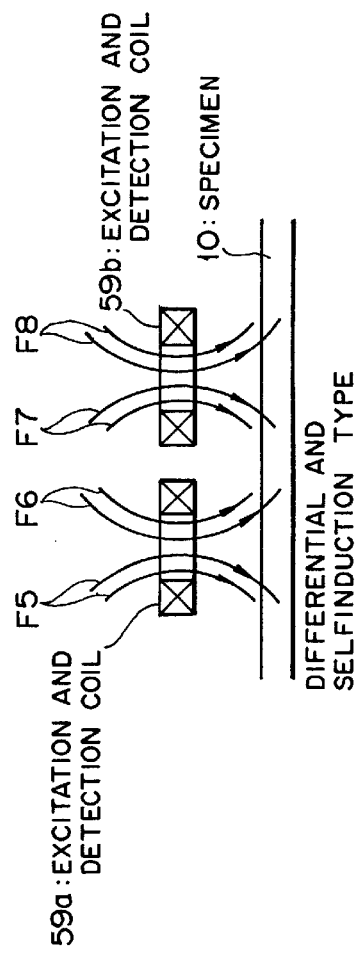
FIG. 7(a) is a schematic diagram illustrating the construction of the conventional eddy current testing probe of the absolute and selfinduction type.
Figure 7B:
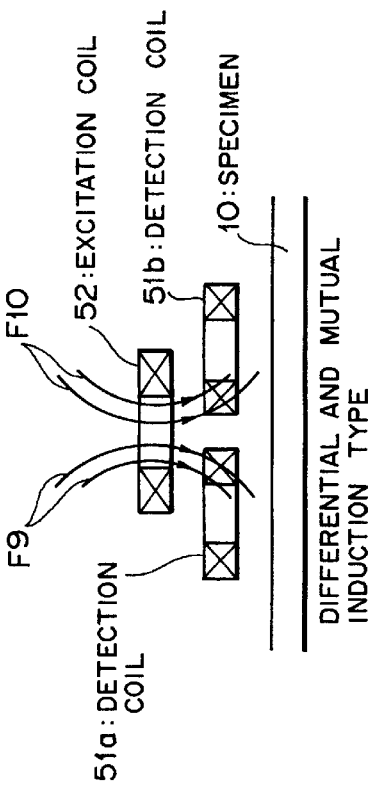
FIG. 7(b) is a schematic diagram illustrating the construction of the conventional eddy current testing probe of the absolute and mutual induction type.
Figure 7C:
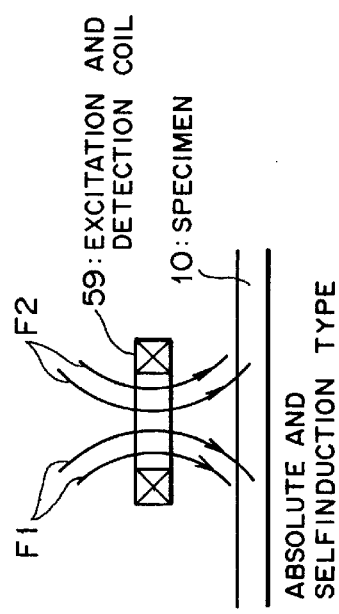
FIG. 7(c) is a schematic diagram illustrating the construction of the conventional eddy current testing probe of the differential and selfinduction type.
Figure 7D:
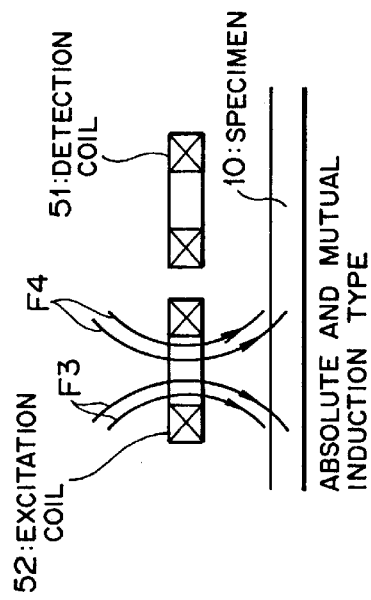
FIG. 7(d) is a schematic diagram illustrating the construction of the conventional eddy current testing probe of the differential and mutual induction type.
Figure 8:
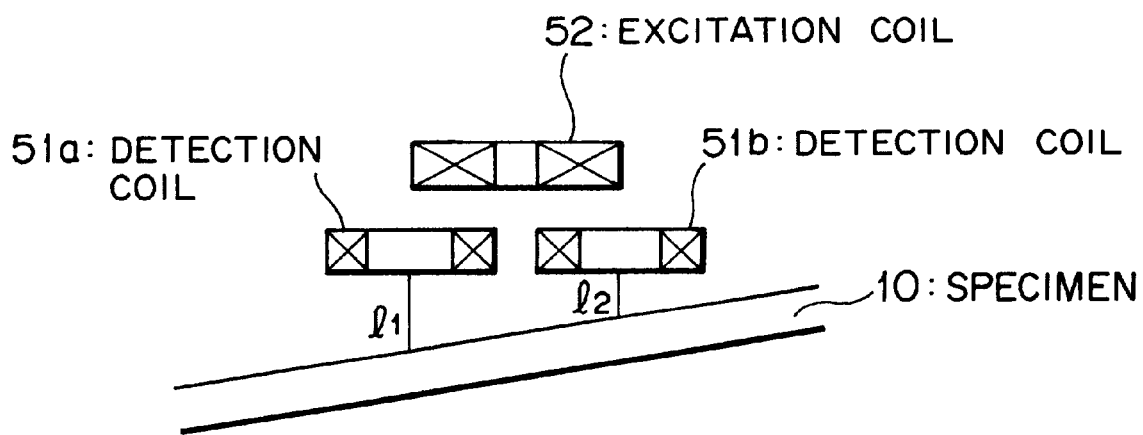
FIG. 8 is a diagram for indicating the problem of the conventional differential-type eddy current testing probe.
Figure 9:
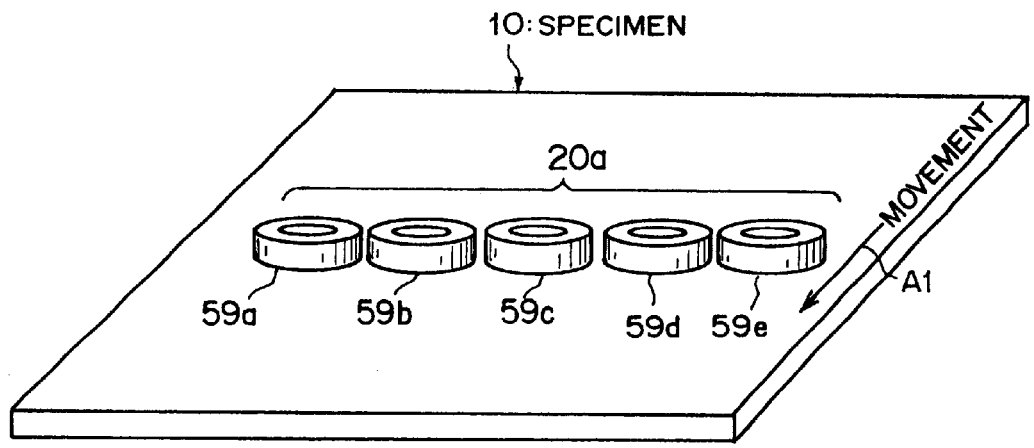
FIG. 9 is a perspective view schematically illustrating the construction of he conventional single-row selfinduction-type multicoil eddy current testing probe.
Figure 10:
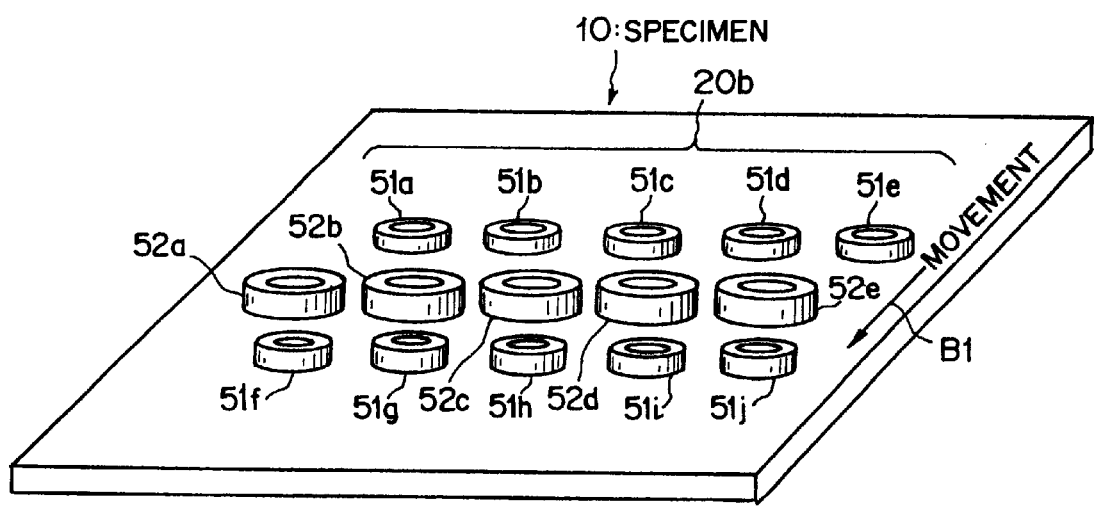
FIG. 10 is a perspective view schematically illustrating the construction of he conventional single-row mutual-induction-type multicoil eddy current testing probe.
Figure 11A:
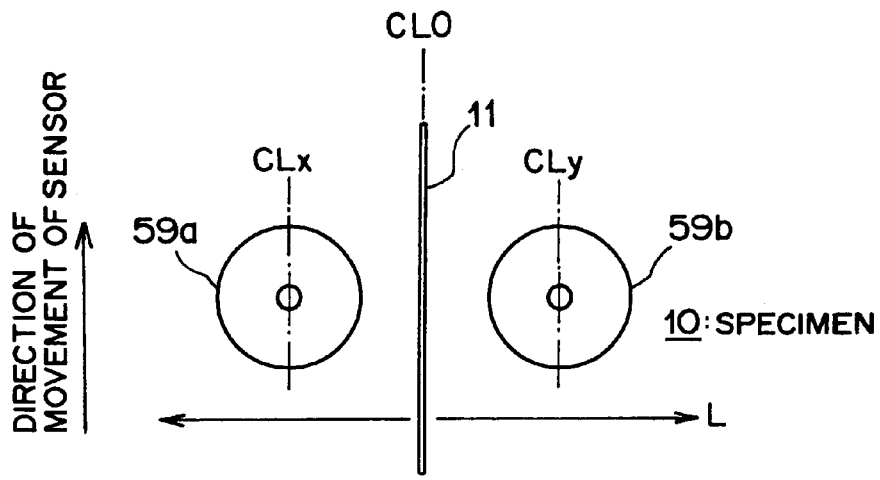
FIG. 11(a) is a plan view schematically illustrating geometrical relationship of a flaw and excitation and detection coils of the conventional single-row selfinduction-type multicoil eddy current testing probe.
Figure 11B:
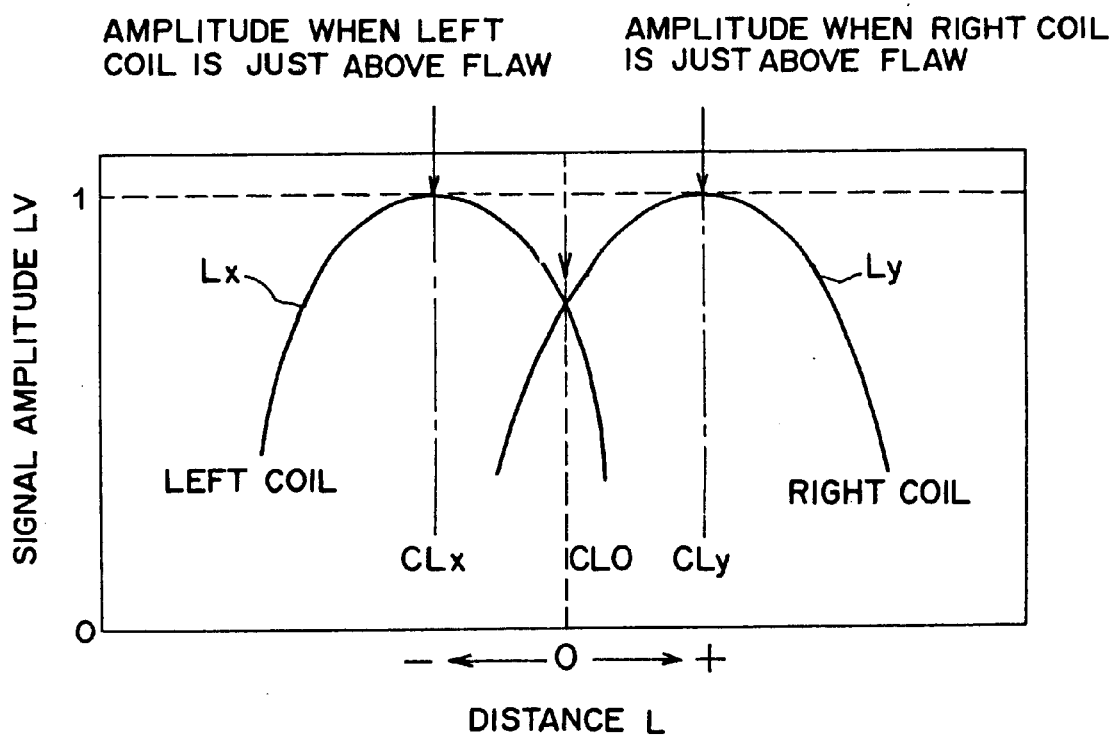
FIG. 11(b) is a diagram illustrating amplitudes of detection signals generated by detection by the excitation and detection coils (i.e., a distribution of detectivity) of the conventional single-row selfinduction-type multicoil eddy current testing probe.
Figure 12:
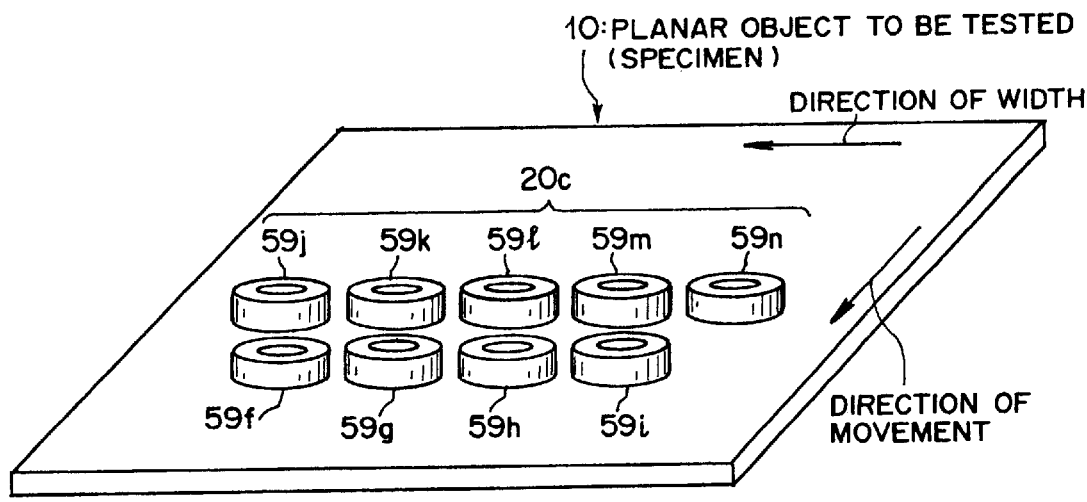
FIG. 12 is a perspective view schematically illustrating the construction of he conventional two-row selfinduction-type multicoil eddy current testing probe.

Next, explanations are provided for the second embodiment. FIGS. 5(a) to 5(c), and 6 relate to the eddy current testing probe as the second embodiment of the present invention, FIGS. 5(a) to 5(c) are schematic diagrams illustrating the construction of the eddy current detection probe, and FIG. 6 shows a distribution of detectivity of the eddy current testing probe.

The eddy current testing probe of the present embodiment is a multicoil eddy current testing probe. As illustrated in FIGS. 5(a) to 5(c), the eddy current testing probe of the present embodiment contains a plurality (eight, in the illustrated example) of thin-film detection coils 21a to 21h arranged in upper and lower layers in a row, and a plurality (eight, in the illustrated example) of excitation coils 22a to 22h arranged in a row above the thin-film detection coils 21a to 21h. Detection of a flaw of the specimen 10 is performed by moving the eddy current testing probe in the direction as indicated by the arrow A4 in FIG. 5(a).

In the following explanations, when it is not necessary to distinguish the thin-film detection coils 21a to 21h or excitation coils 22a to 22h, the thin-film detection coils 21a to 21h may be referred to as detection coils 21, and the excitation coils 22a to 22h may be referred to as excitation coils 22.

Further detailed explanations on the excitation coils 22 are provided below. Each of the excitation coils 22a to 22h is constituted by a circular coil (cf. FIG. 4(c)) having a short length in the direction of the axis, and is arranged so that the round face of the excitation coil stands on the specimen 10 almost perpendicularly, as illustrated in FIG. 5(b). In addition, the excitation coils 22a to 22h are respectively rotated by an identical angle around their axis centerlines which are perpendicular to the specimen 10, so the round faces of the excitation coils 22a to 22h are oriented in a slanting direction with respect to the direction of the row of the excitation coils 22a to 22h. When the excitation coils 22a to 22h are arranged as above, spatially dense probe configuration and efficient excitation can be realized. In addition, due to the above arrangement of the excitation coils 22a to 22h, the size of the eddy current testing probe can be reduced in the direction of movement, compared with the case wherein the round face of the excitation coils 22a to 22h are arranged to be perpendicular to the direction of the row of the excitation coils 22a to 22h. That is, the above arrangement of the excitation coils 22a to 22h enables downsizing of the eddy current testing probe.

An oscillator (not shown) is connected to each of the excitation coils 22a to 22h. When voltages are applied from the oscillator to the excitation coils 22a to 22h, the excitation coils 22a to 22h generate eddy currents in the specimen 10.

If eddy currents 12 are concurrently generated by mutually adjacent ones of the excitation coils 22, 22, these eddy currents 12, 12 interact with each other. Therefore, it is necessary to prevent the concurrent generation of the eddy currents 12 by adjacent ones of the excitation coils 22, 22. In this example, the concurrent applying of the voltages to adjacent ones of the excitation coils 22 is avoided by applying pulsed voltages to the respective excitation coils 22a to 22h.

Next, explanations on the detection coils 21 are provided below. When voltages are applied to the excitation coils 22, eddy currents are generated on the specimen 10 by the action of the excitation coils 22. When a flaw exists on the specimen 10, the flaw affects the state of the eddy currents, and thereby voltages are induced in the detection coils 21. The detection coils 21 are connected to a detection device (not shown) through signal wires 24a so that the voltages generated in the detection coils 21 can be detected as signals indicating the shape of the flaw. FIG. 5(c) shows a portion of the signal wires 24a corresponding to only one side of the detection coil 21h.

In addition, the plurality of detection coils 21a to 21h are arranged in upper and lower layers as stated above. Since the detection coils 21a to 21d in the upper layer are located close to the detection coils 21e to 21h in the lower layer, as illustrated in FIGS. 5(b) and 5(c), an insulation film (thin-film insulation layer) 23 is provided between the detection coils 21a to 21d in the upper layer and the detection coils 21e to 21h in the lower layer so that the detection coils 21a to 21d in the upper layer and the detection coils 21e to 21h in the lower layer do not interact with each other. In this example, the detection coils 21a to 21h are realized by forming spiral metal thin-films on the insulation film 23. Since the detection coils 21a to 21h and the insulation film 23 are extremely thin, it is difficult to illustrate these elements in the actual proportion. Therefore, these elements are enlarged in the vertical direction (in the direction of thickness) in FIG. 5(b), and are further enlarged in FIG. 5(c).

The signals generated in the detection coils 21 vary with the distances between the detection coils 21 and the flaw, i.e., due to the lift-off. However, since all of the detection coils 21a to 21d in the upper layer, the detection coils 21e to 21h in the lower layer, and the insulation film 23 are layered as thin films, almost no difference arises in lift-off between the detection coils 21a to 21d in the upper layer and the detection coils 21e to 21h in the lower layer.

In addition, as illustrated in FIG. 5(c), a plurality of through holes 24 are provided in the insulation film 23 and the detection coils 21a to 21d in the upper layer for leading detection signals out from the detection coils 21e to 21h in the lower layer. (In FIG. 5(b), the through holes 24 are not shown.) Since the detection coils 21 are formed as the spiral metal thin films as described before, the through holes 24 are located in gaps between the spiral metal thin films forming the detection coils 21a to 21h. Each of the through holes 24 are formed by perforating the insulation film 23 and laying conductive metal on the inside surfaces of the perforations.

Portions of the through holes 24 in the detection coils 21a to 21d in the upper layer are formed by providing, in advance, pads (not shown) having thickness corresponding to the thickness of the detection coils 21a to 21d in the upper layer, on the upper side of the insulation film 23 at locations corresponding to the through holes 24, and processing the pads at the same time as the perforation of the insulation film 23 and the laying of the metal on the inside surfaces of the perforations.

Since the upper ends of the through holes 24 reach the upper surfaces of the detection coils 21a to 21d in the upper layer, one end of each of the signal wires 24 provided for the detection coils 21e to 21h in the lower layer can be easily connected to the upper portion of the corresponding one of the through holes 24. (Only the portion of the signal wires 24a corresponding to one side of the detection coil 21h is shown;) The other end of each of the signal wires 24 is connected to a detection circuit (not shown). The laying of the metal on the inside surfaces of the through holes 24 can be performed by vacuum evaporation or plating.

Generally, if signal wires 24a for the detection coils 21e to 21h in the lower layer are led out from the underside of the detection coils 21e to 21h, space for the signal wires is required on the underside of the detection coils 21e to 21h in the lower layer. However, this space becomes unnecessary when the signal wires are led out upward from the through holes 24, and thus it is possible to put the detection coils 21a to 21h closer to the specimen 10. In addition, since the signal wires 24a, which are conductive, are not arranged between the detection coils 21e to 21h in the lower layer and the specimen 10, accuracy of the detection by the detection coils 21 is not degraded.

When it is possible to fill the through holes 24 with conductive metal, it is possible to enhance conductivity between the detection coils 21e to 21h in the lower layer and the signal wire 24a by filling the through holes 24 with conductive metal and connecting the signal wire 24a with the filled metal.

The positions of the detection coils 21a to 21d in the upper layer are relatively shifted by about a half pitch from the positions of the detection coils 21e to 21h in the lower layer. FIG. 6 shows distributions of detectivity of the detection coils 21a, 21e, and 21f among the detection coils 21a to 21h illustrated in FIGS. 5(a) to 5(c), where the abscissa indicates the distance L from the axis centerline CLa, and the ordinate indicates a signal amplitude (signal level) LV which is detected by the detection coil 21a, 21e, or 21f when a flaw exists at the location of the abscissa. The curves La, Le, and Lf indicate distributions of detectivity of the detection coils 21a, 21e, and 21f, respectively. The signal level of the detection coil 21e is maximized when the flaw is located just below the detection coil 21e, i.e., when the flaw is located on the axis centerline CLe. Therefore, the curve Le of the distribution of detectivity of the detection coil 21e has its maximum on the axis centerline CLe. Similarly, the curve La of the distribution of detectivity of the detection coil 21a has its maximum on the axis centerline CLa, and the curve Lf of the distribution of detectivity of the detection coil 21f has its maximum on the axis centerline CLf.

Since the detection coil 21a is layered over the detection coils 21e and 21f at the position relatively shifted by about a half pitch from the positions of the detection coils 21e and 21f, for example, a valley between the curve Le of the distribution of detectivity of the detection coil 21e and the curve Lf of the distribution of detectivity of the detection coil 21f is covered by the detection coil 21a as illustrated by the curve La of the distribution of detectivity of the detection coil 21a in FIG. 6, so that the low-detectivity-level region of the multicoil eddy current testing probe is reduced. That is, detection in the low-detectivity-level region located between the detection coils 21e and 21f in the lower layer is performed by the detection coil 21a in the upper layer. Thus, the distribution of detectivity is flattened.

As described above, when detection coils are arranged in upper and lower layers, it is advantageous that the positions of the detection coils in the upper layer are relatively shifted by a half pitch from the positions of the detection coils in the lower layer for enhancing detectivity through the entire length of the multicoil eddy current testing probe. However, it is still advantageous to a certain degree that the positions of the detection coils in the upper layer are relatively shifted by nearly a half pitch from the positions of the detection coils in the lower layer.

Since the eddy current testing probe as the second embodiment of the present invention is constructed as above, detection of a flaw on the specimen 10 is performed by moving the eddy current testing probe in the direction indicated by the arrow A4 in FIG. 5(a) on the specimen 10. An oscillator (not shown) applies pulsed voltages to the respective excitation coils 22a to 22h, and eddy currents are generated in the specimen 10 corresponding to the applied voltages. If a flaw exists on the specimen 10, the state of the eddy currents varies by an influence of the flaw to induce voltages in the detection coils 21a to 21h. Therefore, the flaw can be detected by monitoring the induced voltages by a detection device (not shown) connected to the respective detection coils 21a to 21h.

In addition, since, in the eddy current testing probe as the second embodiment, the detection coils 21a to 21h are arranged in the upper and lower layers, and the positions of the detection coils 21a to 21d in the upper layer are relatively shifted by a half pitch from the positions of the detection coils 21e to 21h in the lower layer, detection in the low-detectivity-level regions located between adjacent ones of the detection coils 21e to 21h in the lower layer is performed by the detection coils 21a to 21d in the upper layer as their high-detectivity-level regions, and thus the flaw can be detected further accurately due to flattening of the distribution of detectivity.

Figure 13:
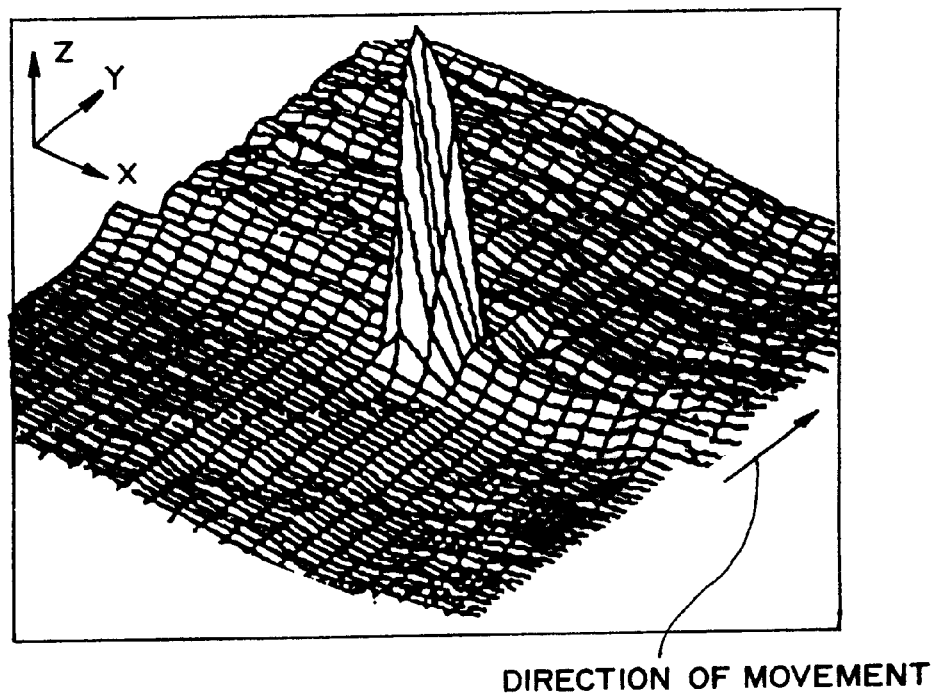
FIG. 13 is a perspective view illustrating a shape of a flaw in a specimen, which is produced based on detection values of the eddy current testing probe.

Further, regarding the location in the direction of movement of the eddy current testing probe, the detection coils 21a to 21d in the upper layer are located exactly over the detection coils 21e to 21h in the lower layer to form a row, data (detection values) at the same location in the direction of movement are concurrently obtained from both the upper layer and the lower layer. Therefore, correction for positions between the data of the detection coils 21a to 21d in the upper layer and the data of the detection coils 21e to 21h in the lower layer is unnecessary, and thus a perspective view which indicates the shape of the flaw as shown in FIG. 13 can be easily produced.

Furthermore, since all of the detection coils 21a to 21d in the upper layer, the detection coils 21e to 21h in the lower layer, and the insulation film 23 are layered as thin films, almost no difference arises in lift-off between the detection coils 21a to 21d in the upper layer and the detection coils 21e to 21h in the lower layer. Therefore, correction for positions between the data of the detection coils 21a to 21d in the upper layer and the data of the detection coils 21e to 21h in the lower layer is unnecessary.

Since the signal wires 24a are led upward from the through holes 24, space for the signal wires 24a is unnecessary on the underside of the detection coils 21e to 21h in the lower layer, and thus it is possible to put the detection coils 21a to 21h closer to the specimen 10 (and the flaw). Detection signals (flaw signals) detected by the detection coils 21a to 21h attenuate with increase in the distances between the detection coils 21a to 21h and the flaw. Since the detection coils 21a to 21h can be put closer to the specimen 10 (flaw), it is possible to suppress the attenuation of the detection signals. In addition, since the signal wires 24a, which are conductive, are not arranged between the specimen 10 and the detection coils 21e to 21h in the lower layer, accuracy of the detection by the detection coils 21 is not degraded.

In addition, pulsed voltages are applied to the respective excitation coils 22a to 22h so as to avoid concurrent application of the voltages to adjacent ones of the excitation coils 22. Therefore, it is possible to prevent interaction between eddy currents which are concurrently generated at adjacent positions, and it is also possible to protect the flaw signals generated by the detection coils 21 corresponding to variation of the eddy currents, from unnecessary external disturbance. Thus, accuracy of detection can be maintained.

Furthermore, since each of the excitation coils 22a to 22h is arranged so that the round face of the excitation coil 22a to 22h stands on the specimen 10 almost perpendicularly, and is oriented in a slanting direction with respect to the direction of the row of the excitation coils 22a to 22h, spatially dense probe configuration and efficient excitation can be realized. In addition, the above arrangement of the excitation coils 22a to 22h enables downsizing of the eddy current testing probe, and therefore handleability of the eddy current testing probe is enhanced.

Although the detection coils 21 are arranged in two layers in the above embodiment, the number of the layers of the detection coils 21 may not be two. For example, the detection coils 21 may be arranged in three layers. In this case, it is most effective to arrange the detection coils 21 so that locations of detection coils in each layer are relatively shifted from locations of detection coils in adjacent layers by one-third of the pitch of detection coils. However, it is also effective to a certain degree if the locations of detection coils in each layer are relatively shifted from the locations of detection coils in adjacent layers by nearly one-third of the pitch of detection coils.

In addition, although the excitation coils 22 are circular coils in this embodiment, the excitation coils 22 may be, for example, rectangular coils as illustrated in FIG. 4(b), or oval coils.

The eddy current testing probes according to the present invention are not limited to the eddy current testing probes of the embodiments described above. Although a planar specimen 10 is subject to the testing in the above embodiments, for example, cylindrical specimens such as pipes can also be tested. In this case, external surfaces of the cylindrical specimen can be tested, for example, by rotating the cylindrical specimen around its axis under the eddy current testing probe.

Industrial Applicability

According to the present invention, even if parallel or tilted lift-off occurs, a flaw on a specimen can be detected based on a difference between voltages generated detection coils due to flux linkages, where the parallelism between the respective detection coils and the specimen are maintained in the parallel lift-off, and the distances from the respective detection coils to the specimen become different in the tilted lift-off. Otherwise, due to provision of a plurality of thin-film detection coils arranged in upper and lower layers in a row, correction, for positions in a direction of movement of the eddy current testing probe (perpendicular to the row) or in an vertical direction, is unnecessary between detection values of detection coils in the upper layer and detection values of detection coils in the lower layer, and thus a flaw on the specimen can be detected easily and accurately.

Therefore, when the present invention is used in nondestructive tests, which are performed, for example, during manufacturing of steel and nonferrous products or maintenance of heat exchanger tubes in various plants, it is possible to improve quality of steel and nonferrous products, and prevent accidents due to damages of various plants. Thus, usability of the-present invention is very high.

What is claimed is:

1. An eddy current flaw detector comprising:
   a pair of excitation coils which generates an alternating magnetic filed to generate an eddy current in a specimen; and
   a pair of detection coils differentially connection and arranged in phase;
   wherein a central portion of the pair of detection coils and a central portion of the pair of excitation coils are arranged to be located at an identical or an almost identical position in a plan view taken in a direction toward the specimen, and a flaw on the specimen is detected based on a difference between voltages generated in the pair of detection coils due to the eddy current.

2. An eddy current flaw detector according to claim 1, wherein the excitation coil generates the eddy current in a slanting direction with respect to a direction of the flaw on the specimen.

3. An eddy current flaw detector according to claim 1, wherein the detection coils in the pair are arranged on a plane, side by side, and symmetrically with respect to a line.

4. An eddy current flaw detector according to claim 1, further comprising a bridge circuit which is connected to the pair of detection coils for obtaining as a flaw signal the difference between voltages generated in the pair of detection coils due to the eddy current.

5. An eddy current flaw detector according to claim 2, wherein the detection coils in the pair are arranged on a plane, side by side, and symmetrically with respect to a line.

6. An eddy current flaw detector according to claim 2, further comprising a bridge circuit which is connected to the pair of detection coils for obtaining as a flaw signal the difference between voltages generated in the pair of detection coils due to the eddy current.

7. An eddy current flaw detector for detecting a flaw on a specimen comprising:
   a plurality of excitation coils for generating an alternating magnetic field to generate an eddy current in the specimen while the specimen is moved relatively with respect to said detector; and
   a plurality of thin-film detection coil rows, said each thin-film detection coil row comprises a plurality of thin-film detection coils which are arranged in a row along the specimen, for detecting a flaw on the specimen based on said eddy current generated by said plural excitation coils;
   said plural thin-film detection coil rows arranged one over another,
   and a centerline of each of said plural thin-film detection coil rows extending in an alignment with the centerline of any of the remaining thin-film detection coil rows in the plan view.

8. An eddy current flaw detector according to claim 7, wherein said individual thin-film detection coils of one of the rows are relatively shifted by about a half pitch from the other row if the number of said thin-film detection coil rows is two.

9. An eddy current flaw detector according to claim 7, wherein a thin-film insulating layer is inserted between adjacent ones of said thin-film detection coil rows.

10. An eddy current flaw detector according to claim 7, wherein each of the excitation coils is realized by a circular coil having a small length in an axis direction and being arranged to stand almost perpendicularly to a surface of the specimen, and the plurality of excitation coils are arranged in one or more rows above the plurality of thin-film detection coils.

11. An eddy current flaw detector according to claim 7, wherein voltages are not applied concurrently to adjacent ones of the plurality of excitation coils.

12. An eddy current flaw detector according to claim 7, being moved along a surface of the specimen in a direction perpendicular to a direction of extending of said plural thin-film detection coil rows, to detect a flaw at the surface of the specimen.

13. An eddy current flaw detector according to claim 8, wherein a thin-film insulating layer is inserted between adjacent ones of said thin-film detection coil rows.

14. An eddy current flaw detector according to claim 8, wherein each of the excitation coils is realized by a circular coil having a small length in an axis direction and being arranged to stand almost perpendicularly to a surface of the specimen, and the plurality of excitation coils are arranged in one or more rows above the plurality of thin-film detection coils.

15. An eddy current flaw detector according to claim 8, wherein voltages are not applied concurrently to adjacent ones of the plurality of excitation coils.

16. An eddy current flaw detector according to claim 8, being moved along a surface of the specimen in a direction perpendicular to a direction of extending of said plural thin-film detection coil rows, to detect a flaw at the surface of the specimen.

17. An eddy current flaw detector according to claim 9, wherein said insulation layer has a through hole for leading out a signal wire of each detection coil in the lower thin-film detection coil row.

18. An eddy current flaw detector according to claim 10, wherein said each of the excitation coils is oriented in a slanting direction with respect to a direction of extending of the layers of the plurality of excitation coils.

19. An eddy current flaw detector according to claim 11, wherein said voltages are applied to the excitation coils in a pulsed mode.

20. An eddy current flaw detector according to claim 13, wherein said insulation layer has a through hole for leading out a signal wire of each detection coil in the lower thin-film detection coil row.

21. An eddy current flaw detector according to claim 14, wherein said each of the excitation coils is oriented in a slanting direction with respect to a direction of extending of the layers of the plurality of excitation coils.

22. An eddy current flaw detector according to claim 15, wherein said voltages are applied to the excitation coils in a pulsed mode.

23. An eddy current flaw detector according to claim 1, wherein the pair of detection coils and the pair of excitation coils are arranged so that a centerline of symmetry of the detection coils is perpendicular to a centerline of symmetry of the excitation coils in the plan view of the specimen.

24. An eddy current flaw detector for detecting a flaw on a specimen comprising:

means for generating an alternating magnetic field to generate an eddy current in the specimen while the specimen is moved relatively with respect to said detector; and a plurality of thin-film detection coil rows, said each thin-film detection coil row comprises a plurality of thin-film detection coils which are arranged in a row along the specimen, for detecting a flaw on the specimen based on said eddy current generated by said generating means;

said plural thin-film detection coil rows arranged one over another, and a centerline of each of said plural thin-film detection coil rows extending in alignment with the centerline of those of any of the remaining thin-film detection coil rows in the plan view.

* * * * *